United States Patent
Heymes et al.

(10) Patent No.: US 11,684,633 B2
(45) Date of Patent: Jun. 27, 2023

(54) POLYDEXTROSE FOR THE PREVENTION AND/OR TREATMENT OF HEART FAILURE

(71) Applicants: VAIOMER, Labege (FR); INSTITUT NATIONAL DE LA SANTE ET DE LA RECHERCHE MEDICALE (INSERM), Paris (FR)

(72) Inventors: Christophe Heymes, Toulouse (FR); Rémy Burcelin, Toulouse (FR); Benjamin Lelouvier, Toulouse (FR); Jacques Amar, Toulouse (FR)

(73) Assignees: VAIOMER, Labege (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 0 days.

(21) Appl. No.: 17/141,891

(22) Filed: Jan. 5, 2021

(65) Prior Publication Data
US 2021/0154217 A1    May 27, 2021

Related U.S. Application Data

(63) Continuation of application No. 15/779,968, filed as application No. PCT/EP2016/079091 on Nov. 29, 2016, now abandoned.

(30) Foreign Application Priority Data

Nov. 30, 2015 (EP) .................................... 15306893

(51) Int. Cl.
*A01N 43/04* (2006.01)
*A61K 31/70* (2006.01)
*A61K 31/715* (2006.01)
*A61P 9/04* (2006.01)
*A61K 31/702* (2006.01)
*A61P 9/10* (2006.01)
*A61K 9/00* (2006.01)

(52) U.S. Cl.
CPC .......... *A61K 31/715* (2013.01); *A61K 9/0019* (2013.01); *A61K 31/702* (2013.01); *A61P 9/04* (2018.01); *A61P 9/10* (2018.01)

(58) Field of Classification Search
None
See application file for complete search history.

(56) References Cited

U.S. PATENT DOCUMENTS

2012/0107291 A1\*  5/2012  Burcelin .............. A61K 31/155
                                                            424/93.4

OTHER PUBLICATIONS

Jie, Zhong, et al. "Studies on the effects of polydextrose intake on physiologic functions in Chinese people." The American journal of clinical nutrition 72.6 (2000): 1503-1509.\*

\* cited by examiner

*Primary Examiner* — Patrick T Lewis
(74) *Attorney, Agent, or Firm* — B. Aaron Schulman, Esq.; Stites & Harbison, PLLC (57) ABSTRACT

A method is provided for preventing and/or treating heart failure in a subject in need thereof by administering to the subject a therapeutically effective amount of polydextrose. The method may also include the use of polydextrose for preventing cardiac remodeling and/or ventricle dilatation and/or for preventing systolic dysfunction, as well as preventing an increase in bacterial translocation to heart tissue in a subject who suffered from a myocardial infarction.

16 Claims, 8 Drawing Sheets

POLYDEXTROSE FOR THE PREVENTION AND/OR TREATMENT OF HEART FAILURE

CROSS-REFERENCE TO RELATED APPLICATIONS

This application is a continuation of U.S. application Ser. No. 15/779,968, having a filing date of May 30, 2018, which is a 371 application of International Patent Application PCT/EP2016/079091, filed on Nov. 29, 2016, which claims the benefit of EP 15306893.7, filed Nov. 30, 2015, all of said applications incorporated herein by reference.

FIELD OF THE INVENTION

The present invention concerns the prevention and/or treatment of heart failure, more particularly of heart failure of ischemic origin.

BACKGROUND OF THE INVENTION

Half of the heart failure cases are of ischemic origin. When administered in acute phase of myocardial infarction, angiotensin-converting-enzyme inhibitors and beta blockers have been demonstrated as having a beneficial effect, in particular on cardiac remodeling. However, despite substantial progresses, the prognosis of patients suffering from heart failure due to ischemic cardiopathy is not good, since the five-year mortality year is 50%.

Additionally, because of the improvement in the survival rate after myocardial infarction, there is an increase in the incidence of heart failure after a myocardial infarction. For example, it has been demonstrated in the large study in the Canadian population, that 36% of the patients hospitalized with a myocardial infarction developed a heart failure de novo during their hospitalization and 50% of the remaining patients developed a heart failure de novo within 1 year after the myocardial infarction occurred.

Accordingly, there is an important need of preventing and treating heart failure, in particular heart failure of ischemic origin.

The present invention arises from the unexpected finding by the inventors that polydextrose, when administered before or after an ischemic event, could have a beneficial effect on cardiac remodeling and function after the ischemic event, thereby preventing or treating a subsequent heart failure. More particularly, they showed that polydextrose treatment was associated with favorable hemodynamic and structural consequences with a decrease in the left ventricular dilation, an increase in the shortening fraction, an increase in the left ventricular ejection fraction and a decrease in the left ventricular end-diastolic pressure.

The inventors demonstrated that this beneficial effect was associated with a modification in the bacterial translocation to the heart, which is observed further to the ischemic event.

The present invention thus concerns polydextrose for use for preventing and/or treating heart failure in a subject.

The present invention also concerns polydextrose for use for preventing cardiac remodeling and/or ventricle dilatation and/or for preventing systolic dysfunction.

The present invention also concerns a method for preventing an increase in bacterial translocation to heart tissue in a subject who suffered from a myocardial infarction, comprising administering to said subject an effective amount of polydextrose.

DETAILED DESCRIPTION OF THE INVENTION

Heart Failure

As used herein, the term "heart failure" refers to a condition wherein the heart, via an abnormality of cardiac function (detectable or not), fails to pump blood at a rate commensurate with the requirements of the metabolizing tissues or is able to do so only with an elevated diastolic filling pressure. Heart failure may be chronic or acute.

Preferably, in the context of the invention, the heart failure to be treated or prevented is acute heart failure.

Acute heart failure is defined as the rapid onset of symptoms and signs of heart failure secondary to abnormal cardiac function.

The heart failure may involve the left ventricle, the right ventricle or both. Accordingly, the heart failure to be treated or prevented in the context of the invention may be selected from left heart failure, right heart failure and global heart failure.

Furthermore, heart failure is generally divided into two different types: heart failure due to reduced ejection fraction (also known as heart failure with ventricular systolic dysfunction) and heart failure with preserved ejection fraction (also known as heart failure with preserved ventricular systolic function or diastolic heart failure).

Accordingly, the heart failure to be treated or prevented in the context of the invention may be selected from the group consisting of heart failure with ventricular systolic dysfunction and heart failure with preserved ventricular systolic function.

More particularly, the heart failure to be treated or prevented in the context of the invention may be selected from the group consisting of heart failure with left ventricular systolic dysfunction, heart failure with preserved left ventricular systolic function and right heart failure.

Heart failure, in particular acute heart failure, may be due to multiple causes and precipitating factors, such as decompensation of pre-existing chronic heart failure (e.g. cardiomyopathy); acute coronary syndromes including myocardial infarction, unstable angina with large extent of ischemia and ischemic dysfunction, mechanical complication of acute myocardial infarction and right ventricular infarction; hypertensive crisis, acute arrhythmia including ventricular tachycardia, ventricular fibrillation, atrial fibrillation or flutter and other supraventricular tachycardia; valvular regurgitation including endocarditis, rupture of chordae tendinae and worsening of pre-existing valvular regurgitation; severe aortic valve stenosis; acute severe myocarditis; cardiac tamponade; aortic dissection; post-partum cardiomyopathy; and non-cardiovascular precipitating factors including lack of compliance with medical treatment, volume overload, infections particularly pneumonia or septicaemia, severe brain insult, after major surgery, reduction in renal function, asthma, drug abuse, alcohol abuse and phaeochromocytoma.

Preferably, the heart failure, in particular the acute heart failure, to be treated or prevented in the context of the invention is of ischemic origin. More preferably, the heart failure, in particular the acute heart failure, to be treated or prevented in the context of the invention is due to myocardial infarction. Most preferably, the heart failure, in particular the acute heart failure, to be treated or prevented in the context of the invention is heart failure with left ventricular systolic dysfunction due to myocardial infarction.

Alternatively, the heart failure, in particular the acute heart failure, to be treated or prevented in the context of the invention is of non-ischemic origin. It may in particular be heart failure with left ventricular systolic dysfunction of non-ischemic origin or post-adriamycin chemotherapy heart failure.

Subject

In the context of the present invention, a "subject" denotes a human or non-human mammal, such as a rodent (rat, mouse, rabbit), a primate (chimpanzee), a feline (cat), or a canine (dog). Preferably, the subject is human. The subject according to the invention may be in particular a male or a female.

In a particular embodiment of the invention, the subject is at risk of heart failure.

Preferably, the subject suffered from a myocardial infarction.

Polydextrose

As used herein, the term "polydextrose" refers to a low calorie polymer of glucose, which is resistant to digestion by the enzymes in the stomach. It includes polymers products of glucose which are prepared from glucose, maltose, oligomers of glucose or hydrolysates of starch, which are polymerized by heat treatment in a polycondensation reaction in the presence of an acid, e.g. Lewis acid, inorganic acid or organic acid, including monocarboxylic acid, dicarboxylic acid and polycarbolxylic acid, such as the products prepared by the processes described in the U.S. Pat. Nos. 2,436,967, 2,719,179, 4,965,354, 3,766,165, 5,051,500, 5,424,418, 5,378,491, 5,645,647, 5,773,604 and 6,475,552.

The term "polydextrose" also includes the polymer products of glucose prepared by the polycondensation of glucose, maltose, oligomers of glucose or starch hydrolyzates in the presence of a sugar alcohol, e.g. polyol, such as in the reactions described in the U.S. Pat. No. 3,766,165.

Moreover, the term "polydextrose" includes the glucose polymers which have been purified by techniques described in the art, such as (a) neutralizing any acid associated therewith by base addition thereto, or by passing a concentrated aqueous solution of the polydextrose through an adsorbent resin, a weakly basic ion exchange resin, a type II strongly basic ion-exchange resin, mixed bed resin comprising a basic ion exchange resin or a cation exchange resin, as described in U.S. Pat. Nos. 5,667,593 and 5,645,647; or (b) decolorizing by contacting the polydextrose with activated carbon or charcoal, by slurrying or by passing the solution through a bed of solid adsorbent or by bleaching with sodium chlorite, hydrogen peroxide, or the like; (c) molecular sieving methods, like ultrafiltration, reverse osmosis, size exclusion and the like; (d) enzymatically treating polydextrose; or (e) any other recognized techniques known in the art. Among the purification processes used in the art, the following may be especially mentioned: bleaching e.g. using hydrogen peroxide; membrane technology; ion exchange e.g. removal of citric acid as described in U.S. Pat. No. 5,645,647, or removal of color/bitter taste; chromatographic separation with a strong cation exchanger; hydrogenation in combination with ion exchange or with ion exchange and chromatographic separation, as described in U.S. Pat. No. 5,424,418; or solvent extraction.

The term "polydextrose" further includes hydrogenated polydextrose, which, as used herein, includes hydrogenated or reduced polyglucose products prepared by techniques known from the skilled person, such as techniques described in U.S. Pat. Nos. 5,601,863, 5,620,871 or 5,424,418.

The term "polydextrose" also encompasses fractionated polydextrose, which is a conventional, known material and can be produced e.g. by the processes disclosed in the U.S. Pat. No. 5,424,418.

In a preferred embodiment, the polydextrose is purified polydextrose. In another preferred embodiment, the polydextrose is hydrogenated or reduced polydextrose. In a particularly preferred embodiment, the polydextrose is both purified and hydrogenated.

It is preferred that the polydextrose used is substantially pure. The polydextrose may be made substantially pure using conventional techniques known from the skilled person, such as chromatography, including column chromatography, HPLC and the like. It is particularly preferred that the polydextrose used is at least 80% pure, i.e. at least about 80% of the impurities are removed. More preferably, it is at least 85% pure or even more preferably at least 90% pure.

Medical Use

The present invention concerns polydextrose, as defined in the section "Polydextrose" above for use for preventing and/or treating heart failure, as defined in the section 'Heart failure" above, in a subject, as defined in the section "Subject" above.

The present invention further concerns the use of polydextrose, as defined in the section "Polydextrose" above, in the manufacture of a medicament intended for the prevention and/or the treatment of heart failure, as defined in the section "Heart failure" above, in a subject, as defined in the section "Subject" above.

Another object of the invention concerns a method of preventing and/or treating heart failure, as defined in the section "Heart failure" above, in a subject, as defined in the section "Subject" above, in need thereof, comprising administering to said subject a therapeutically effective amount of polydextrose, as defined in the section "Polydextrose" above.

In the context of the invention, the term "treating" or "treatment", as used herein, means reversing, alleviating, inhibiting the progress of the disorder or condition to which such term applies, or one or more symptoms of such disorder or condition.

"Preventing" refers to measures taken to prevent the disorder or condition to which such term applies from occurrence or, in early stages of a disease or disorder.

A "therapeutically effective amount" refers to a quantity of active agent that confers a therapeutic effect on the treated subject. The therapeutic effect may be objective (i.e. measurable by some test or marker) or subjective (i.e. subject gives an indication of or feels an effect). As known from the skilled person, effective doses will vary depending on route of administration, the size and/or weight of the subject, as well as the possibility of co-usage with other agents.

Any suitable method of administration known from one skilled in the art may be used. In particular, polydextrose may be administered for example by the oral route.

Polydextrose for oral administration may be in the form of, for example, aqueous or oily suspensions, solutions, emulsions, syrups or elixirs, or may be presented as a dry product for constitution with water or other suitable vehicle before use. Such liquid pharmaceutical compositions may contain conventional additives such as suspending agents, emulsifying agents, non-aqueous vehicles (which may include edible oils), or preservatives.

Polydextrose may be included in pharmaceutical compositions further containing excipients such as flavorings, colorings, anti-microbial agents, or preservatives.

The dose range depends on the composition to be administered. As is well known in the medical arts, dosages for any one subject depend on many factors, including the patient's size, body surface area, age, the particular compound to be administered, sex, time and route of administration, general health, and other drugs being administered concurrently. Preferably, polydextrose is administered at a dose of 12 g to 90 g per day.

In the context of the invention, polydextrose is preferably administered to the subject to be treated after myocardial infarction occurred, more preferably as soon as possible after myocardial infarction occurred. In particular, polydextrose may be administered to the subject to be treated 1 to 12 hours after myocardial infarction occurred, 1 day after myocardial infarction occurred, 2 days after myocardial infarction occurred or even 3 days after myocardial infarction occurred.

Alternatively, polydextrose can be administered before occurrence of myocardial infarction, in particular in subjects at risk of myocardial infarction, and can optionally still be administered after the occurrence of myocardial infarction. In a particular embodiment, polydextrose is administered in a subject at risk of myocardial infarction.

By "subject at risk of myocardial infarction" is meant herein a subject displaying known risk factors of occurrence of myocardial infarction. Such risk factors are well-known from the skilled person and include obesity, smoking, diabetes, high blood pressure, hyperlipidemia and family history of myocardial infarction.

The present inventors demonstrated more particularly that administration of polydextrose in a model of myocardial infarction enabled significantly improving the end-diastolic and end-systolic volumes, which showed a prevention of ventricle, in particular left ventricle, dilatation.

They also showed that administration of polydextrose in the same model enabled significantly decreasing left ventricular end-diastolic pressure, improving developed pressure and improving cardiac contractility parameters such as contraction (+dP/dtmax) and relaxation (dP/dtmin).

The present invention thus further concerns polydextrose, as defined in the section "Polydextrose" above for use for preventing and/or treating heart failure, as defined in the section 'Heart failure" above, in a subject, as defined in the section "Subject" above, for preventing cardiac remodeling and/or ventricle dilatation.

The present invention further concerns the use of polydextrose, as defined in the section "Polydextrose" above, in the manufacture of a medicament intended for the prevention and/or the treatment of heart failure, as defined in the section "Heart failure" above, in a subject, as defined in the section "Subject" above, for the prevention of cardiac remodeling and/or ventricle dilatation.

Another object of the invention concerns a method of preventing cardiac remodeling and/or ventricle dilatation in a subject, as defined in the section "Subject" above, in need thereof, comprising administering to said subject a therapeutically effective amount of polydextrose, as defined in the section "Polydextrose" above.

As used herein, "ventricle dilatation" refers to an increase in size of ventricular cavity. Ventricular dilatation can typically be determined by measuring end-diastolic and end-systolic volumes by techniques well-known from the skilled person. It can also be represented by the ejection fraction which is the ratio between the stroke volume (difference between the end-diastolic volume and the end-systolic volume) and the end-diastolic volume: a reduced ejection fraction indicates ventricle dilatation.

Ventricle dilatation is more particularly observed in cases of heart failure with ventricular systolic dysfunction. Accordingly, in a particular embodiment, polydextrose is for use for preventing ventricle dilatation for treating and/or preventing heart failure with ventricular systolic dysfunction.

As used herein, "cardiac remodeling" or "ventricular remodeling" refers to the changes in size, shape, structure and physiology of the heart after injury to the myocardium.

The present invention thus further concerns polydextrose, as defined in the section "Polydextrose" above for use for preventing and/or treating heart failure, as defined in the section 'Heart failure" above, in a subject, as defined in the section "Subject" above, for preventing systolic dysfunction.

The present invention further concerns the use of polydextrose, as defined in the section "Polydextrose" above, in the manufacture of a medicament intended for the prevention and/or the treatment of heart failure, as defined in the section "Heart failure" above, in a subject, as defined in the section "Subject" above, for the prevention of systolic dysfunction.

Another object of the invention concerns a method of preventing systolic dysfunction in a subject, as defined in the section "Subject" above, in need thereof, comprising administering to said subject a therapeutically effective amount of polydextrose, as defined in the section "Polydextrose" above.

As used herein, "systolic dysfunction" refers to ventricular failure characterized by a reduced ejection fraction and an enlarged ventricular chamber.

The present inventors demonstrated that polydextrose treatment modify the intestinal and cardiac tissue microbiota in a myocardial infarction murine model and prevents notably the increase in bacterial DNA in cardiac tissues in acute phase of infarction in mice The present invention thus further concerns a method for preventing an increase in bacterial translocation to heart tissue in a subject who suffered from a myocardial infarction, comprising administering to said subject an effective amount of polydextrose, as defined in the section "Polydextrose" above.

As used herein, "bacterial translocation" refers to the passage of viable bacteria from the gastrointestinal tract to extraintestinal sites.

In the context of the invention, polydextrose may be administered in combination with conventional therapies of heart failure, in particular of acute heart failure, and/or post-myocardial infarction.

Conventional therapies of heart failure and/or post-myocardial infarction are well-known from the skilled person and include morphine and its analogues, anticoagulation therapy, vasodilators including nitrates, sodium nitroprusside, nesiritide and calcium antagonists, angiotensin converting enzyme inhibitors, diuretics, p-blocking agents, inotropic agents including dopamine, dobutamine, phosphodiesterase inhibitors, levosimendan and cardiac glycosides.

The present invention will be further illustrated by the figures and examples below.

BRIEF DESCRIPTION OF THE FIGURES

FIG. 1 shows the left ventricular end-diastolic volume (in $cm^3$) of hearts of:

mice which underwent a thoracotomy but no coronary ligation (Sham), mice which were treated with polydextrose 7 days before the surgery and during 28 days after the thoracotomy without coronary ligation (Sham+PBS d−7), mice which underwent a thoracotomy with coronary ligation (MI), mice which underwent a thoracotomy with coronary ligation and were treated with polydextrose 7 days before and during 28 days after the surgery (MI+PDX d−7), and mice which underwent a thoracotomy with coronary ligation and were treated with polydextrose 3 days after and during 25 days after the operation (MI+PDX d+3), as disclosed in the example below.

FIG. 1 demonstrated that administration of PDX, before and after left coronary ligation, ameliorates significantly left ventricular dilation (estimated by left ventricular end-diastolic volume), as compared with the MI group.

a: $P<0.05$ versus Sham; b: $P<0.05$ versus MI.

FIG. 2 demonstrated that administration of PDX, before and after left coronary ligation, ameliorates significantly left ventricular dilation (estimated by left ventricular end-systolic volume), as compared with the MI group.

a: $P<0.05$ versus Sham; b: $P<0.05$ versus MI.

FIG. 3 demonstrated that PDX treatment both prevented or rescued the decrease of cardiac function, estimated by the % of ejection fraction, following 28 days of MI.

a: $P<0.05$ versus Sham; b: $P<0.05$ versus MI.

FIG. 4 demonstrated that administration of PDX, before and after left coronary ligation, ameliorates significantly the decreased left ventricular end-diastolic pressure observed in the MI group.

a: $P<0.05$ versus Sham; b: $P<0.05$ versus MI.

FIG. 5 demonstrated that administration of PDX, before and after left coronary ligation, ameliorates significantly the decreased developed pressure observed in the MI group.

a: $P<0.05$ versus Sham; b: $P<0.05$ versus MI.

FIG. 6 demonstrated that administration of PDX, before and after left coronary ligation, ameliorates significantly both the decreased cardiac contractility (estimated by the LV dP/dtmax index) and relaxation (estimated by the LV dP/dt-min index) observed in the MI group.

a: $P<0.05$ versus Sham; b: $P<0.05$ versus MI.

FIG. 7 demonstrated that MI surgery induced a significant increase in bacterial translocation both in the blood and the heart of operated mice.

a: $P<0.05$ versus Sham 12 h post-surgery; b: $P<0.05$ versus Sham 1 day post-surgery; c: $P<0.05$ versus Sham 3 days post-surgery.

a: P<0.05 versus NF.

EXAMPLE

The inventors carried out an experimental study in mice in a murine model of myocardial infarction.

Materials and Methods

Treatment of Mice

Five groups of mice were formed.

The first control group of mice (Sham) underwent a thoracotomy but no coronary ligation.

The second group of mice (Sham+PDX) was treated with polydextrose 7 days before and during 28 days after the thoracotomy (without coronary ligation).

The third group of mice (MI) underwent a thoracotomy with coronary ligation.

The fourth group of mice (MI+PDX d−7) underwent a thoracotomy with coronary ligation and was treated with polydextrose 7 days before and during 28 days after the surgery.

The fifth group of mice (MI+PDX d+3) underwent a thoracotomy with coronary ligation and was treated with polydextrose 3 days after and during 25 days after the surgery.

The treatment with polydextrose was administered daily by gavage (0.2 g/mice/day).

Polydextrose used was Litesse Ultra polydextrose commercialized by Dupont.

Cardiac Surgery

Myocardial infarction (MI) was performed on 8 week-old male C57BL/6J. In brief, male 8 week-old mice were anesthetized by an intraperitoneal (i.p.) injection of a cocktail of ketamine (100 mg/kg) and xylazine (10 mg/kg), intubated, and connected to a mouse ventilator (MiniVent, Harvard Apparatus, Holliston, Mass.). Permanent ligation of the left anterior descending artery was blocked using a segment of saline 9-0 prolene. The sham group (without ligation of the left anterior descending artery) was set up as the control group. All surgical procedures were performed under sterile conditions. Successful cardiac infarction was confirmed by apparent S-T segment elevation. 4 weeks post-surgery, echocardiography and left ventricular catheter were performed; subsequently, cardiac tissues from different regions were harvested for further analysis.

Echocardiography

Non-invasive ultrasound examination of the cardiovascular system was performed using a General Electric instrument equipped with a linear 8-14-MHz transducer. The surgeon and echocardiographer were blinded to animal genotype.

Hemodynamic Analysis Using Intraventricular Catheterization

Adult mice were anesthetized in order to produce a near physiologic heart rate of 500 beats/min. The mice were intubated and ventilated with a Harvard ventilator set at 200-400 μl. The bilateral carotid arteries were identified in the region of the trachea and the right carotid was cannulated with a 1.0 French mouse pressure catheter (Millar, SPR-1000). The catheter was advanced retrogradely through the aortic valve into the left ventricle to assess pressure volume loops. LV systolic and diastolic pressures, the derivative of LV pressure (dP/dT), and tau were recorded and analysed with Emka analysis software (iox2).

Measurement of Blood Concentration of the Bacterial Gene Encoding the 16S Ribosomal RNA Total bacterial DNA was extracted from snap-frozen feces, blood and cardiac tissue specimen using the QIAamp DNA mini stool kit (Qiagen, Courtaboeuf, France), which also included homogenization using a (≤106 μm diameter) bead-beating step (6,500 rpm, 3×30 s). The inventors studied the 16S rDNA gene as some regions of this gene are highly conserved between different species of bacteria and it is considered a marker of the overall microbiota. The 16S rDNA sequences that belong to the Proteobacteria phylum (Pbac) were measured. The DNA was amplified by real-time PCR (Stepone+; Applied Biosystems) in optical grade 96-well plates. The PCR was performed in a total volume of 25 μl using the Power SYBR® Green PCR master mix (Applied Biosystems), containing 300 nM of each of the universal forward and reverse primers.

The deep sequencing of the tissue microbiota was performed by 16S rDNA MiSeq sequencing. 450 bp sequences were obtained and analyzed using Mothur software.

Results

The inventors studied the hemodynamic consequences and the consequences on cardiac remodeling associated with polydextrose treatment (administered preventively or curatively).

Figure 1:
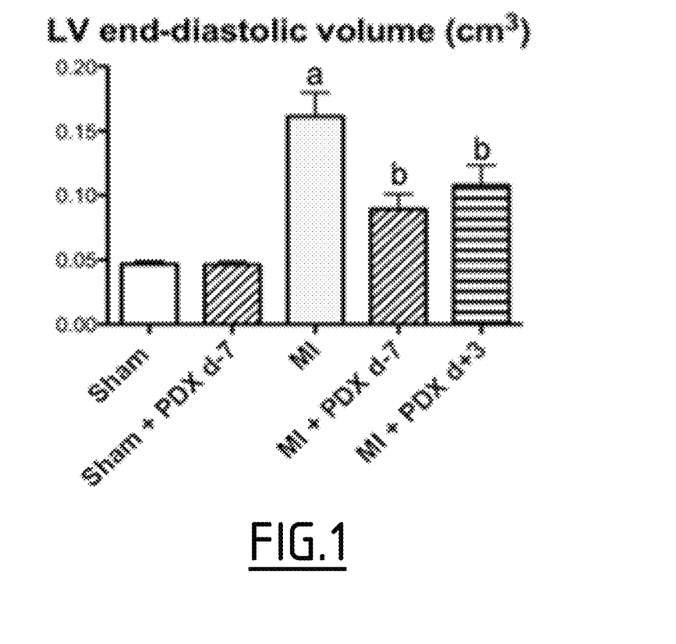
Figure 2:
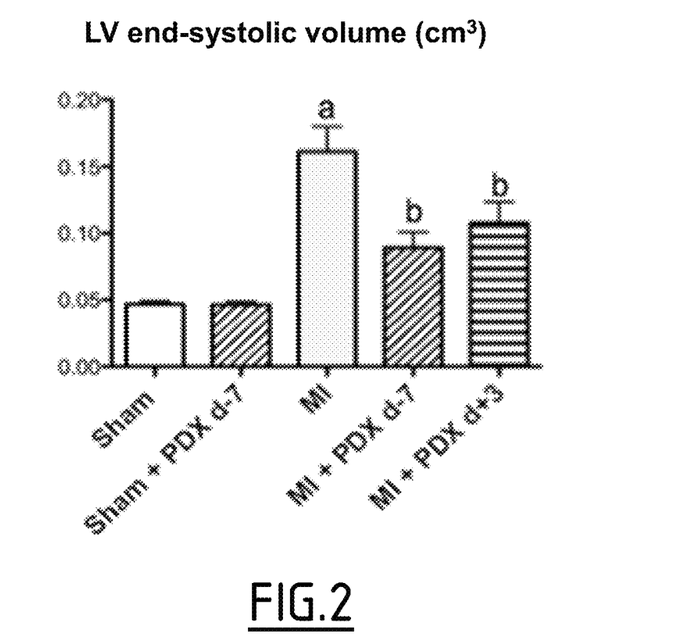
FIG. 2 shows the left ventricular end-systolic volume (in $cm^3$) of hearts of mice which underwent a thoracotomy but no coronary ligation (Sham), mice which were treated with polydextrose 7 days before and during 28 days after the thoracotomy without coronary ligation (Sham+PBS d−7), mice which underwent a thoracotomy with coronary ligation (MI), mice which underwent a thoracotomy with coronary ligation and were treated with polydextrose 7 days before and during 28 days after the surgery (MI+PDX d−7), and mice which underwent a thoracotomy with coronary ligation and were treated with polydextrose 3 days after and during 25 days after the surgery (MI+PDX d+3), as disclosed in the example below.
Figure 3:
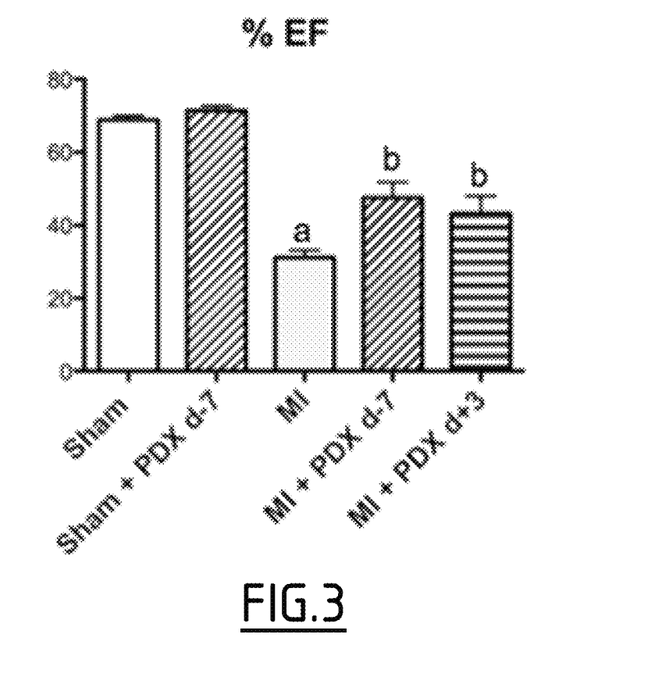
FIG. 3 shows the left ventricular ejection fraction (% EF) of hearts of mice which underwent a thoracotomy but no coronary ligation (Sham), mice which were treated with polydextrose 7 days before and during 28 days after the thoracotomy without coronary ligation (Sham+PBS d−7), mice which underwent a thoracotomy with coronary ligation (MI), mice which underwent a thoracotomy with coronary ligation and were treated with polydextrose 7 days before and during 28 days after the surgery (MI+PDX d−7), and mice which underwent a thoracotomy with coronary ligation and were treated with polydextrose 3 days after and during 25 days after the surgery (MI+PDX d+3), as disclosed in the example below.
Figure 4:
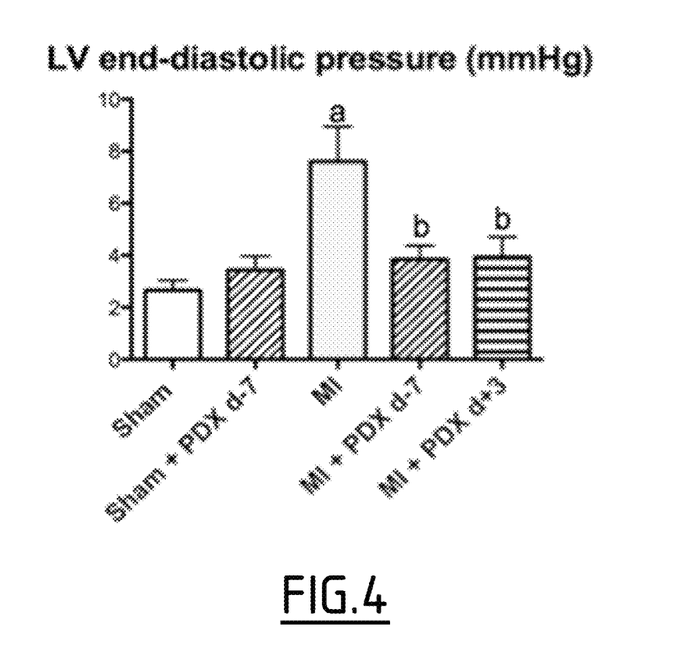
FIG. 4 shows the left ventricular end-diastolic pressure (mmHg) of hearts of mice which underwent a thoracotomy but no coronary ligation (Sham), mice which were treated with polydextrose 7 days before and during 28 days after the thoracotomy without coronary ligation (Sham+PBS d−7), mice which underwent a thoracotomy with coronary ligation (MI), mice which underwent a thoracotomy with coronary ligation and were treated with polydextrose 7 days before and during 28 days after the surgery (MI+PDX d−7), and mice which underwent a thoracotomy with coronary ligation and were treated with polydextrose 3 days after and during 25 days after the surgery (MI+PDX d+3), as disclosed in the example below.
Figure 5:
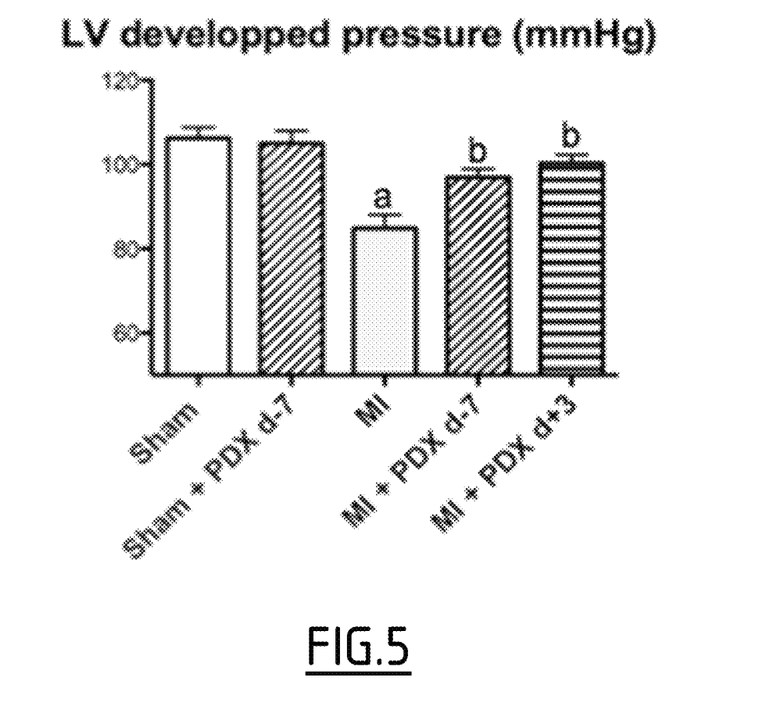
FIG. 5 shows the left ventricular developed pressure (mmHg) of hearts of mice which underwent a thoracotomy but no coronary ligation (Sham), mice which were treated with polydextrose 7 days before and during 28 days after the thoracotomy without coronary ligation (Sham+PBS d−7), mice which underwent a thoracotomy with coronary ligation (MI), mice which underwent a thoracotomy with coronary ligation and were treated with polydextrose 7 days before and during 28 days after the surgery (MI+PDX d−7), and mice which underwent a thoracotomy with coronary ligation and were treated with polydextrose 3 days after and during 25 days after the surgery (MI+PDX d+3), as disclosed in the example below.
Figure 6:
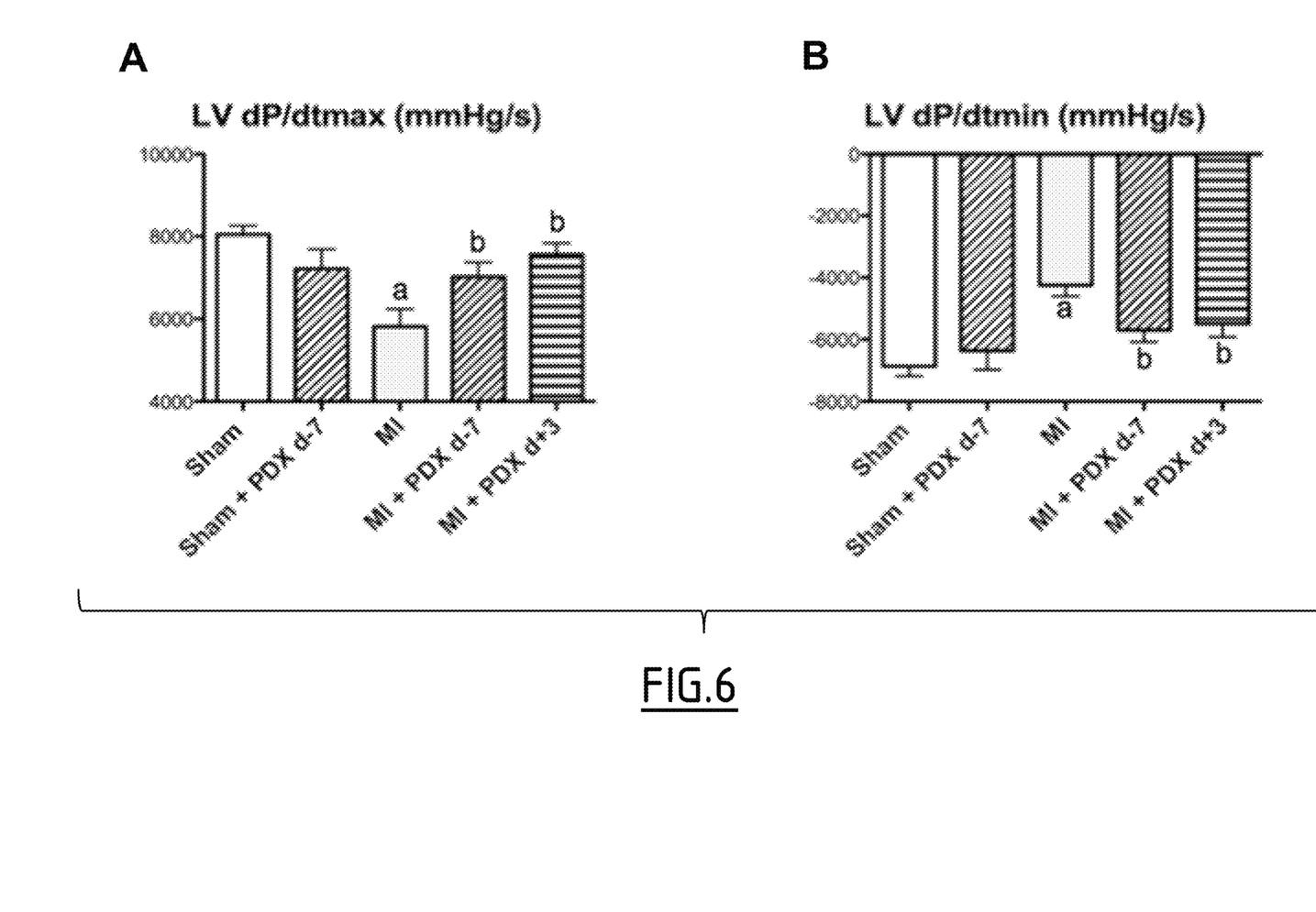
FIG. 6 shows (A) the left ventricular contraction dP/dt-max (mmHg/s) and (B) the left ventricular relaxation dP/dt-min (mmHg/s) of hearts of mice which underwent a thoracotomy but no coronary ligation (Sham), mice which were treated with polydextrose 7 days before and during 28 days after the thoracotomy without coronary ligation (Sham+PBS d−7), mice which underwent a thoracotomy with coronary ligation (MI), mice which underwent a thoracotomy with coronary ligation and were treated with polydextrose 7 days before and during 28 days after the surgery (MI+PDX d−7), and mice which underwent a thoracotomy with coronary ligation and were treated with polydextrose 3 days after and during 25 days after the surgery (MI+PDX d+3), as disclosed in the example below.

They observed, in treated animals compared to non-treated animals, which underwent a myocardial infarction:

by echocardiography: a lesser dilatation of the left ventricular cavity (significant improvement of left ventricular end-diastolic and end-systolic volumes, as shown on FIGS. 1 and 2), associated with a significant improvement of the left ventricular ejection fraction (% EF), as shown on FIG. 3.

by hemodynamic analysis using intraventricular catheterization: a reduction in the left-ventricular end-diastolic pressure, as shown on FIG. 4, an improvement of the left ventricular developed pressure, as shown on FIG. 5, and an improvement in the cardiac contractility parameters (contraction+dP/dtmax and relaxation dP/dtmin), as shown on FIG. 6.

The inventors further studied the intestinal and cardiac tissue microbiota to analyze the effect of polydextrose on bacterial translocation.

Intestinal and cardiac tissue microbiota was analyzed by sequencing the bacterial gene encoding the 16S ribosomal RNA. Blood concentration of the bacterial gene encoding the 16S ribosomal RNA was measured before and after myocardial infarction.

Figure 7:
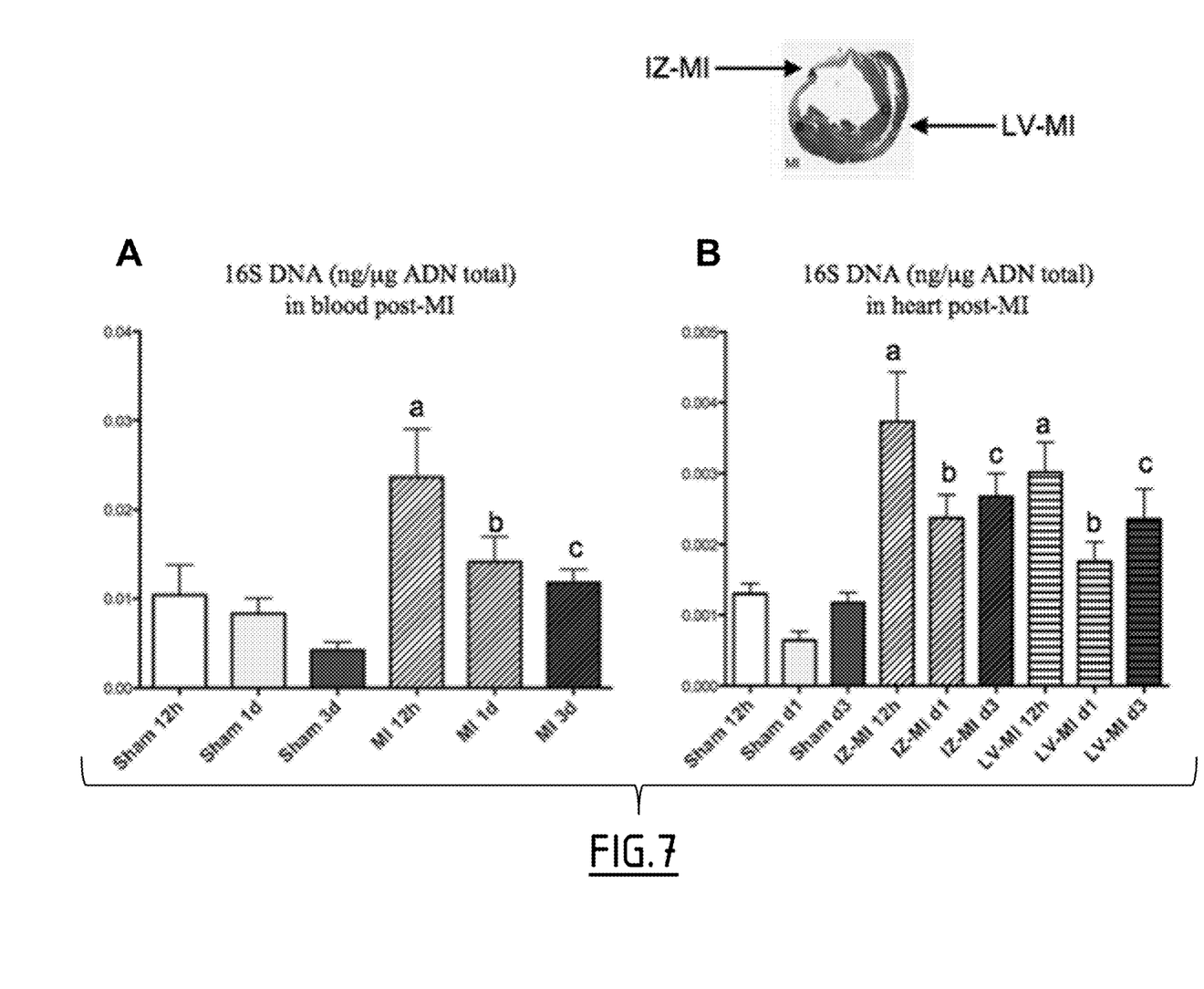
FIG. 7 shows the concentration of bacterial DNA encoding the 16S ribosomal RNA (ng/μg total DNA) in (A) blood or (B) heart of mice which underwent a thoracotomy but no coronary ligation (Sham) or mice which underwent a thoracotomy with coronary ligation (MI), 12 hours, 1 day and 3 days after the operation.

The inventors observed that a myocardial infarction induces a bacterial translocation, as soon as 12 hours post-surgery, in blood and cardiac tissues, with an accumulation of the bacterial level in the infarcted zone (IZ-MI) and in the still living zone of the left ventricle (LV-MI), as shown on FIG. 7.

Figure 8:
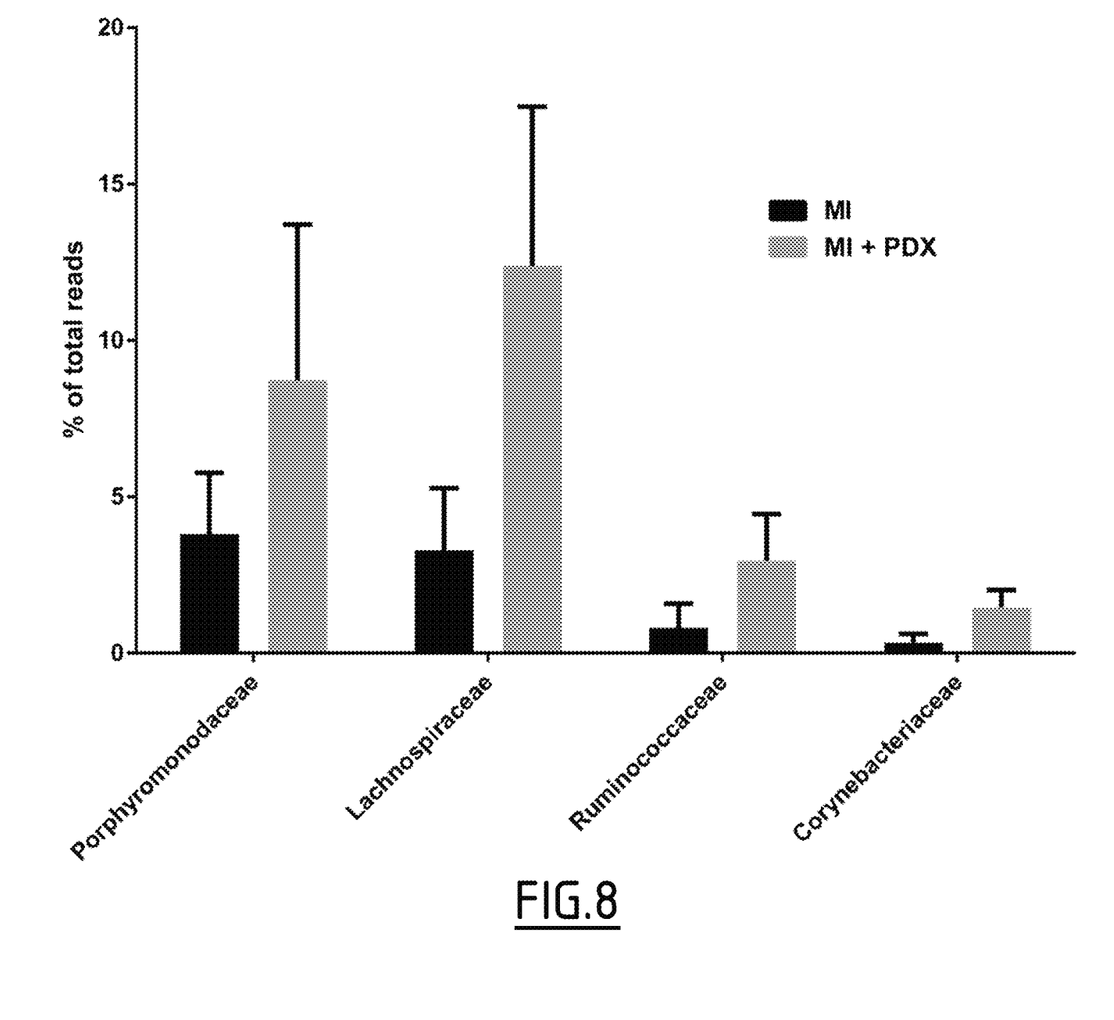
FIG. 8 shows the level (percentage of total reads), determined by targeted metagenomics sequencing, of different bacterial family in the cardiac tissue of mice who underwent a thoracotomy with coronary ligation (MI) and of mice which underwent a thoracotomy with coronary ligation and were treated with polydextrose.
Figure 9:
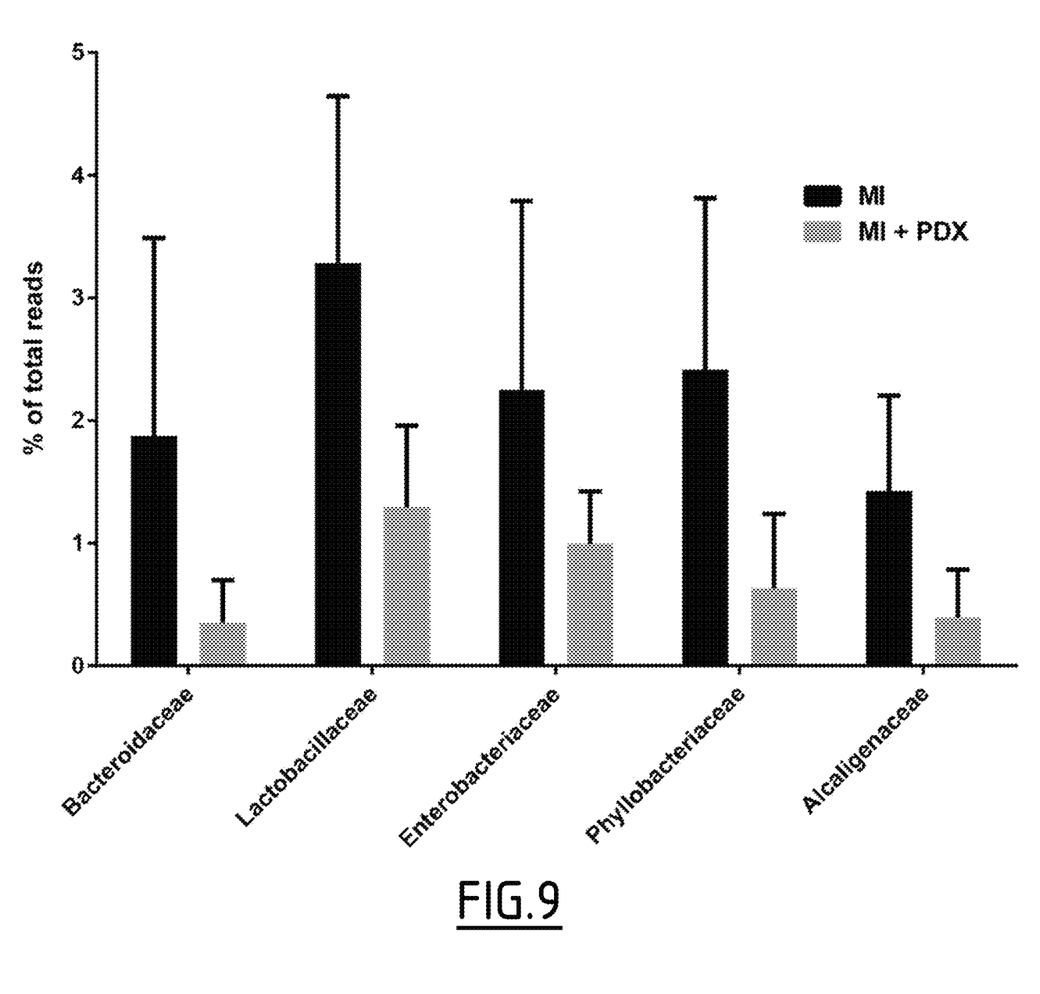
FIG. 9 shows the level (percentage of total reads), determined by targeted metagenomics sequencing, of different bacterial family in the cardiac tissue of mice who underwent a thoracotomy with coronary ligation (MI) and of mice which underwent a thoracotomy with coronary ligation and were treated with polydextrose.

They further observed qualitatively, in untreated mice which underwent a myocardial infarction (MI), a change in the intestinal and cardiac tissue microbiota compared to control animals (Sham). Additionally, polydextrose-treated mice which underwent a myocardial infection (MI+PDX) displayed a different microbiota compared to MI mice, to Sham+PDX mice and to Sham mice. Furthermore, the inventors showed that, quantitatively, polydextrose reduced bacterial translocation in the cardiac tissue in MI+PDX mice compared to MI mice (FIGS. 8 and 9).

Figure 10:
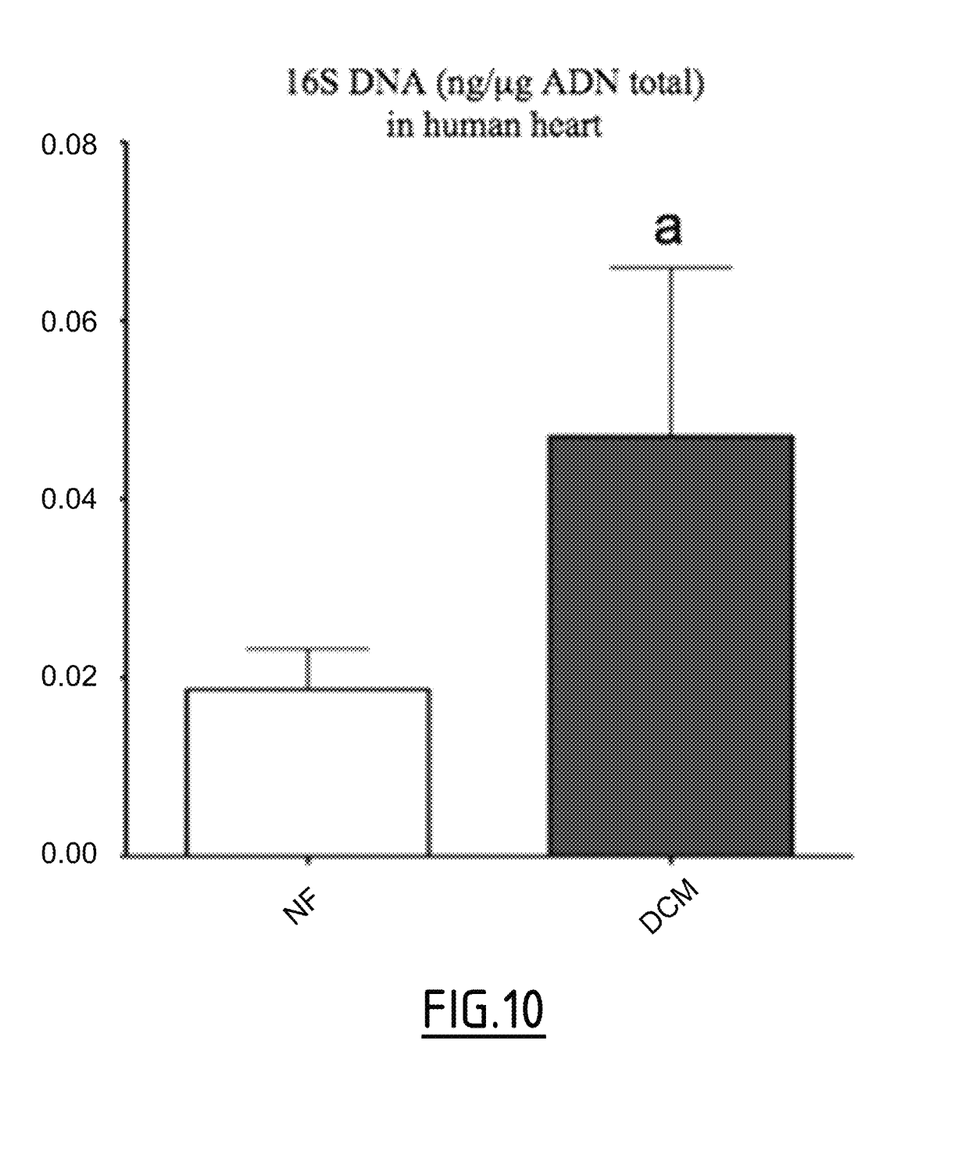
FIG. 10 shows the concentration of bacterial DNA encoding the 16S ribosomal RNA (ng/μg total DNA) in cardiac tissue of hearts from healthy subjects (NF) and from subjects suffering from hypokinetic dilated cardiomyopathy (DCM).

The inventors further measured the concentration of the bacterial gene encoding 16S ribosomal RNA in human cardiac tissues, from hearts withdrawn from heart-transplanted patients suffering from hypokinetic dilated cardiomyopathy or from hearts from healthy donors and intended to be transplanted in patients suffering from heart failure. They showed an increase in the concentration of bacterial DNA encoding 16S ribosomal RNA in hearts from heart-transplanted patients, as shown on FIG. 10.

These results thus show that polydextrose treatment modify the intestinal and cardiac tissue microbiota in a myocardial infarction murine model and prevents notably the increase in bacterial DNA in cardiac tissues in acute phase of infarction in mice. This is associated with favorable hemodynamic and structural consequences with a decrease in the left ventricular dilation, an increase in the shortening fraction, an increase in the left ventricular ejection fraction and a decrease in the left ventricular end-diastolic pressure. The inventors further confirmed the relevance of these results in humans, by demonstrating that an increase in bacterial DNA concentration could be observed in cardiac tissue of hearts from patients suffering from hypokinetic dilated cardiomyopathy.

What is claimed is:

1. A method for preventing and/or treating heart failure in a subject in need thereof, comprising administering to said subject a therapeutically effective amount of a pharmaceutical composition consisting of polydextrose and one or more excipients, wherein said subject suffered from a myocardial infarction.

2. The method according to claim 1, wherein said heart failure is acute heart failure.

3. The method according to claim 1, wherein said heart failure is selected from the group consisting of left heart failure, right heart failure, and global heart failure.

4. The method according to claim 1 wherein said heart failure is selected from the group consisting of heart failure with ventricular systolic dysfunction and heart failure with preserved ventricular systolic function.

5. The method according to claim 1, wherein said heart failure is of ischemic origin.

6. The method according to claim 1, wherein cardiac remodeling and/or ventricle dilatation is prevented.

7. The method according to claim 1, wherein systolic dysfunction is prevented.

8. A method for preventing and/or treating heart failure in a subject in need thereof, comprising administering to said subject a therapeutically effective amount of a pharmaceutical composition consisting of polydextrose and one or more excipients, wherein said subject suffered from a myocardial infarction, and wherein polydextrose is administered to said subject after myocardial infarction occurred.

9. The method according to claim 1, wherein said polydextrose is purified polydextrose.

10. The method according to claim 8, wherein said heart failure is acute heart failure.

11. The method according to claim 8, wherein said heart failure is selected from the group consisting of left heart failure, right heart failure, and global heart failure.

12. The method according to claim 8 wherein said heart failure is selected from the group consisting of heart failure with ventricular systolic dysfunction and heart failure with preserved ventricular systolic function.

13. The method according to claim 8, wherein said heart failure is of ischemic origin.

14. The method according to claim 8, wherein cardiac remodeling and/or ventricle dilatation is prevented.

15. The method according to claim 8, wherein systolic dysfunction is prevented.

16. The method according to claim 8, wherein said polydextrose is purified polydextrose.

* * * * *